United States Patent [19]
Englert et al.

[11] Patent Number: 5,792,788
[45] Date of Patent: Aug. 11, 1998

[54] SUBSTITUTED THIOPHENESULFONYLUREAS AND -THIOUREAS, PROCESSES FOR THEIR PREPARATION, THEIR USE AS A MEDICAMENT OR DIAGNOSTIC, AND MEDICAMENT CONTAINING THEM

[75] Inventors: Heinrich Englert, Hofheim; Jens Hartung, Höchberg; Peter Crause, Offenbach; Dieter Mania, Königstein; Heinz Gögelein; Joachim Kaiser, both of Frankfurt, all of Germany

[73] Assignee: Hoechst Aktiengesellschaft, Frankfurt am Main, Germany

[21] Appl. No.: 593,621

[22] Filed: Jan. 30, 1996

[30] Foreign Application Priority Data

Feb. 1, 1995 [DE] Germany ............... 195 03 136.9

[51] Int. Cl.$^6$ .............. A61K 31/38; C07D 333/32
[52] U.S. Cl. ............................... 514/445; 549/65
[58] Field of Search ..................... 549/65; 514/445

[56] References Cited

U.S. PATENT DOCUMENTS

| 3,124,597 | 3/1964 | Stoll et al. ............. | 549/65 |
| 3,494,936 | 2/1970 | Weger et al. ............ | 549/65 |
| 3,998,968 | 12/1976 | Hitzel et al. ............ | 424/321 |
| 5,476,850 | 12/1995 | Englert et al. .......... | 514/239.5 |

FOREIGN PATENT DOCUMENTS

| 0 612 724 | 8/1994 | European Pat. Off. . |
| 0 657 423 | 6/1995 | European Pat. Off. . |
| 0 661 264 | 7/1995 | European Pat. Off. . |
| 1 940 131 | 2/1971 | France . |
| 1 518 874 | 5/1970 | Germany . |
| 2 068 472 | 8/1971 | Germany . |
| 24 13 514 | 2/1976 | Germany . |
| 70 11 219 | 2/1971 | Netherlands . |
| 1 322 980 | 7/1973 | United Kingdom . |

OTHER PUBLICATIONS

S. Amoroso et al., "Glucose, Sulfonylureas, and Neurotransmitter Release: Role of ATP-Sensitive K+ Channels" Science, vol. 247, (1990) pp. 852–854.

N. Sturgess et al., "The Sulphonylurea Receptor May Be A ATP-Sensitive Potassium Channel" The Lancet, vol. 2, No. 8453, (1955) pp. 474–475.

M. Fosset et al., "Identification, Mécanisms de Fonctionnement et Régulation des Canaux Potassium Sensibles À L'ATP Cibles des Sulfonylurées Utilisées Dans le Traitement du Diabéte de Type II" Jorn. Annu. Diabetol. (1989) pp. 7–11.

Chemical Abstract of DE-B-1 518 874, vol. 82, p. 408, No. 43073m, 1975.

*Primary Examiner*—Deborah C. Lambkin
*Attorney, Agent, or Firm*—Finnegan, Henderson, Farabow, Garrett & Dunner, L.L.P.

[57] ABSTRACT

Substituted thiophenesulfonylureas and -thioureas I

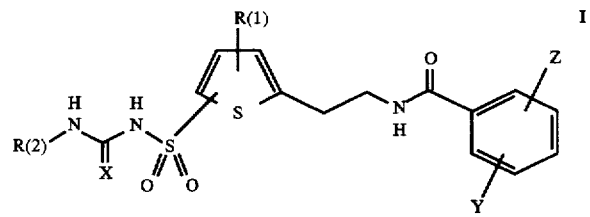

wherein

R(1) is selected from the group consisting of hydrogen, halogen, alkyl having 1 or 2 carbon atoms, alkoxy having 1 or 2 carbon atoms, mercaptoalkyl having 1 or 2 carbon atoms, fluoroalkoxy having 1 or 2 carbon atoms, and fluoroalkyl having 1 or 2 carbon atoms;

R(2) is selected from the group consisting of hydrogen, alkyl having 1 or 2 carbon atoms such as methyl, alkoxy having 1 or 2 carbon atoms, and trifluoromethyl;

X is selected from the group consisting of oxygen (compounds Ia) or sulfur (compounds Ib);

Y and Z are identical or different and are selected from the group consisting of hydrogen, F, Cl, Br, I, alkyl having 1 or 2 carbon atoms and alkoxy having 1 or 2 carbon atoms.

14 Claims, No Drawings

SUBSTITUTED THIOPHENESULFONYLUREAS AND -THIOUREAS, PROCESSES FOR THEIR PREPARATION, THEIR USE AS A MEDICAMENT OR DIAGNOSTIC, AND MEDICAMENT CONTAINING THEM

The invention relates to substituted thiophenesulfonylureas and -thioureas I

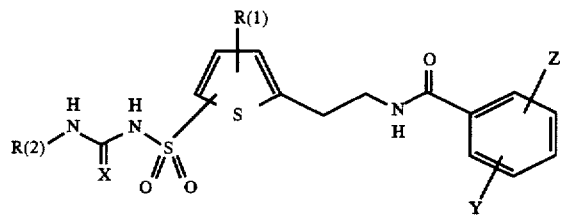

wherein,

R(1) is selected from the group consisting of hydrogen, halogen, alkyl having 1 or 2 carbon atoms, alkoxy having 1 or 2 carbon atoms, mercaptoalkyl having 1 or 2 carbon atoms, fluoroalkoxy having 1 or 2 carbon atoms, and fluoroalkyl having 1 or 2 carbon atoms;

R(2) is selected from the group consisting of hydrogen, alkyl having 1 or 2 carbon atoms such as methyl, alkoxy having 1 or 2 carbon atoms, and trifluoromethyl;

X is selected from the group consisting of oxygen (compounds Ia) or sulfur (compounds Ib);

Y and Z are identical or different and are selected from the group consisting of hydrogen, F, Cl, Br, I, alkyl having 1 or 2 carbon atoms and alkoxy having 1 or 2 carbon atoms.

The halogen substituent employed can be the elements fluorine, chlorine, bromine and iodine. Similar thiophenesulfonylureas are disclosed in the Dutch Patent Application NL 70 11 219; similar benzenesulfonylureas are disclosed in the German Offenlegungsschriften 2 413 514 and 1 518 874. Their hypoglycemic action is described there. A prototype of such hypoglycemic sulfonylureas is glibenclamide, which is used therapeutically as an agent for the treatment of diabetes mellitus and serves in research as a much-regarded tool for the investigation of so-called ATP-sensitive potassium channels. In addition to its hypoglycemic action, glibenclamide additionally has other actions which could not be employed therapeutically until now, but which are all attributed to blockade of precisely these ATP-sensitive potassium channels. This includes, in particular, an antifibrillatory action on the heart. In the treatment of ventricular fibrillation or its preliminary stages, however, a simultaneous lowering of blood sugar would be undesirable or even dangerous since it can further worsen the condition of the patient.

It was therefore the object of the present invention to synthesize compounds which have an equally good cardiac action as glibenclamide, but have no or distinctly less effect on the blood sugar in cardiac-active doses or concentrations than glibenclamide. Sulfonylureas and thioureas having a preferred action on the heart have already been disclosed in European Offenlegungsschrift 0 612 724 (Hoe 93/F 058).

Preferred compounds I are those in which:

R(1) is hydrogen or alkyl having 1 or 2 carbon atoms or alkoxy having 1 or 2 carbon atoms;

R(2) is hydrogen, or methyl; and

X is oxygen or sulfur;

Y and Z are different from one another and are fluorine, chlorine, methoxy or alkoxy.

Particularly preferred compounds I are those in which:

R(1) is hydrogen or alkyl having 1 or 2 carbon atoms;

R(2) is hydrogen or therefore methyl;

X is oxygen;

Y and Z are different from one another and are fluorine, chlorine, methoxy or ethoxy.

Very particularly preferred compounds I are those in which:

R(1) is hydrogen or alkyl having 1 or 2 carbon atoms;

R(2) is hydrogen or therefore methyl;

X is sulfur;

Y and Z are different from one another and are fluorine, chlorine, methoxy or ethoxy.

The compounds of the present invention are useful pharmaceuticals for the treatment of cardiac arrhythmias of all types of origin and for the prevention of sudden heart death due to arrhythmia and can therefore be used as antiarrhythmics. Examples of arrhythmic disorders of the heart are supraventricular arrhythmias such as, for example, atrial tachycardias, atrial flutters or paroxysmal supraventricular arrhythmias or ventricular arrhythmias such as ventricular extrasystoles, but in particular life-threatening ventricular tachycardias or the particularly dangerous ventricular fibrillation. They are suitable in particular for those cases where arrhythmias are the result of a constriction of a coronary vessel, such as occur, for example, in angina pectoris or during an acute cardiac infarct or as a chronic result of a cardiac infarct. They are therefore suitable, in particular, in postinfarct patients for the prevention of sudden heart death. Further syndromes in which arrhythmias of this type and/or sudden heart death due to arrhythmia play a part are, for example, cardiac insufficiency or cardiac hypertrophy as a result of a chronically raised blood pressure.

Moreover, the compounds can positively affect a decreased contractility of the heart. In this context, it can be a question of a disease-related relaxation of cardiac contractility such as, for example, in cardiac insufficiency but also of acute cases such as heart failure in the case of effects of shock. Likewise, in a heart transplantation, the heart, after operation has taken place, can resume its functional capacity more rapidly and more reliably. The same applies to operations on the heart which make necessary a temporary paralysis of heart activity by means of cardioplegic solutions.

The invention furthermore relates to a process for the preparation of the compounds I, which comprises (a) reacting aromatic sulfonamides of the formula II

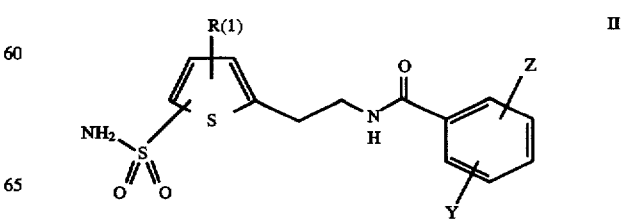

or its salt of the formula III

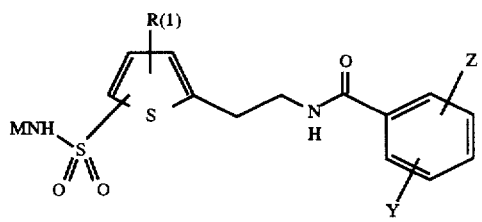

in which R(1), Y, and Z have the meanings indicated above and in which M is an alkali metal, alkaline earth metal, ammonium or tetraalkylammonium ion, with R(2)-substituted isocyanates of the formula IV

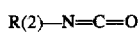

in which R(2) has the meaning indicated above, to give substituted thiophenesulfonylureas I. Equivalently to the R(2)-substituted isocyanates IV, R(2)-substituted carbamic acid esters, R(2)-substituted carbamic acid halides or R(2)-substituted ureas can be employed; or (b) Unsubstituted thiophenesulfonylureas I a wherein R(2) is H

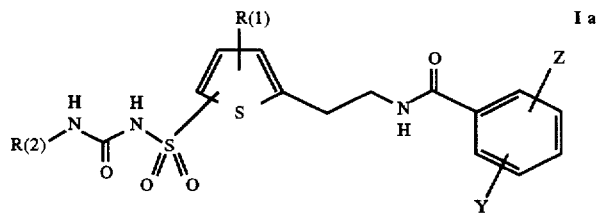

can be prepared by reactions of aromatic thiophenesulfonamides of the formula II or their salts III with trialkylsilyl isocyanate or silicon tetraisocyanate and cleavage (e.g. hydrolysis) of the primary silicon-substituted thiophenesulfonylureas. It is furthermore possible to prepare thiophenesulfonamides II or their salts III by reaction with cyanogen halides and hydrolysis of the N-cyanosulfonamides primarily formed with mineral acids at temperatures from 0° C. to 100° C.

(c) Thiophenesulfonylureas I a can be prepared from aromatic thiophenesulfonamides II or their salts III from R(2)-substituted trichloroacetamides of the formula V

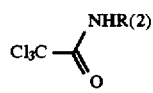

in the presence of a base in an inert solvent according to Synthesis 1987, pp. 734–735 at temperatures from 25° C. to 150° C.

Suitable bases are, for example, alkali metal or alkaline earth metal hydroxides, hydrides, amides or alternatively alkoxides, such as sodium hydroxide, potassium hydroxide, calcium hydroxide, sodium hydride, potassium hydride, calcium hydride, sodium amide, potassium amide, sodium methoxide, sodium ethoxide, potassium methoxide or potassium ethoxide.

Suitable inert solvents are ethers such as tetrahydrofuran, dioxane, ethylene glycol dimethyl ether (diglyme), ketones such as acetone or butanone, nitrites such as acetonitrile, nitro compounds such as nitromethane, esters such as ethyl acetate, amides such as dimethylformamide (DMF) or N-methylpyrrolidone (NMP), hexamethylphosphoramide, sulfoxides such as DMSO, sulfones such as sulfolane, and hydrocarbons such as benzene, toluene and xylenes. Furthermore, mixtures of these solvents with one another are also suitable.

(d) Thiophenesulfonylthioureas Ib

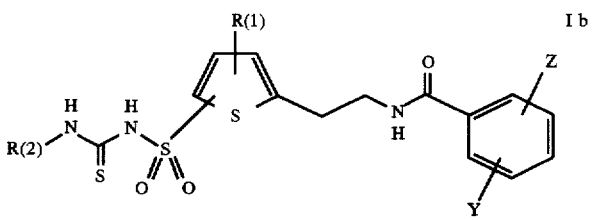

are prepared from thiophenesulfonamides II and their salts III and R(2)-substituted isothiocyanates VI

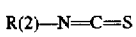

Unsubstituted thiophenesulfonylthioureas I [R(2)=H] can be prepared by reactions of aromatic thiophenesulfonamides II or of their salts III with trimethylsilyl isothiocyanate or silicon tetraisothiocyanate and cleavage (hydrolysis) of the silicon-substituted thiophenesulfonylureas primarily formed. It is furthermore possible to react aromatic thiophenesulfonamides II or their salts II with benzoyl isothiocyanate and to react the intermediate benzoyl-substituted thiophenesulfonylthioureas with aqueous mineral acids to give I b [R(2)=H]. Similar processes are described in *J. Med. Chem.* 1992, 35, pp. 1137–1144. A further variant consists in reacting the N-cyanosulfonamides mentioned under process a with hydrogen sulfide.

e) Substituted thiophenesulfonylureas of the formula I a can be prepared by transformation reactions of thiophenesulfonylthioureas of the structure I b. The replacement of the sulfur atom by an oxygen atom in the correspondingly substituted thiophenesulfonylthioureas can be carried out, for example, with the aid of oxides or salts of heavy metals or alternatively by use of oxidants (such as hydrogen peroxide, sodium peroxide or nitrous acid). Thioureas can also be desulfurized by treatment with phosgene or phosphorus pentachloride. As intermediates, chloroformic acid amidines or carbodiimides are obtained which are converted, for example, by hydrolysis or addition of water into the corresponding substituted thiophenesulfonylureas. Isothioureas behave like thioureas in desulfurization and can accordingly also be used as starting substances for these reactions.

(f) Thiophenesulfonylureas I a can be prepared from thiophenesulfonyl halides of the formula VII

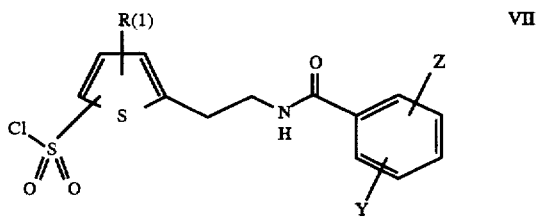

using R(2)-substituted ureas or R(2)-substituted bis (trialkylsilyl)ureas. The trialkylsilyl protective group can be removed from the resulting (trialkylsilyl)-thiophenesulfonylurea by standard methods. Furthermore, the sulfonyl chlorides VII can be reacted with parabanic acids to give thiophenesulfonylparabanic acids, whose hydrolysis with mineral acids yields the corresponding thiophenesulfonylureas I a.

(g) Thiophenesulfonylureas I a can be prepared by reactions of amines of the formula R(2)—NH$_2$ with thiophenesulfonyl isocyanates of the formula VIII

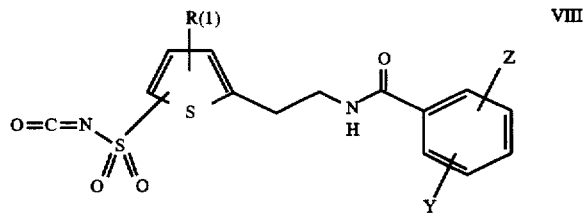

VIII

Likewise, amines R(2)—NH$_2$ can be reacted with thiophene-sulfonylcarbamic acid esters, -carbamic acid halides or thiophenesulfonylureas I a [where R(2)=H] to give the compounds I a.

(h) Thiophenesulfonylthioureas I b can be prepared by reactions of an amine of the formula R(2)—NH$_2$ with a thiophenesulfonyl isothiocyanate of the formula IX

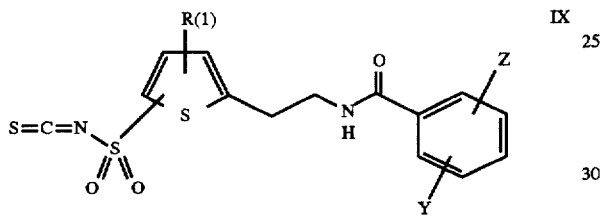

IX

Likewise, amines R(1)—NH$_2$ can be reacted with thiophenesulfonylcarbamic acid thioesters or -carbamic acid thiohalides to give the compounds I b.

(i) Correspondingly substituted benzenesulfenyl- or -sulfinylureas can be oxidized with oxidants such as hydrogen peroxide, sodium peroxide or nitrous acid to give thiophenesulfonylureas I a.

Compounds I and their physiologically acceptable salts are useful therapeutics which are suitable not only as antiarrhythmics, but also for prophylaxis in the case of disorders of the cardiovascular system, in cardiac insufficiency, in heart transplantations or cerebral vascular disorders in humans or mammals (for example apes, dogs, mice, rats, rabbits, guinea-pigs and cats).

Physiologically acceptable salts of the compounds I are understood according to Remmington's Pharmaceutical Science, 17th edition, 1985, pages 14–18 as meaning compounds of the formula X

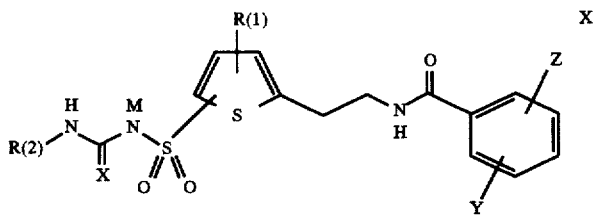

X which can be prepared from nontoxic organic and inorganic bases and substituted thiophenesulfonylureas I. In this context, salts are preferred in which M in the formula X is sodium, potassium, rubidium, calcium, magnesium or ammonium ions, and can be the acid addition products of basic amino acids, such as lysine or arginine.

The starting compounds for the mentioned synthesis processes of the thiophenesulfonylureas I are prepared by known methods, such as are described in the literature (for example in the standard works such as Houben-Weyl, Methoden der Organischen Chemie [Methods of Organic Chemistry], Georg Thieme Verlag, Stuttgart; Organic Reactions, John Wiley & Sons, Inc., New York; and in the patent applications indicated above), namely under reaction conditions which are known and suitable for the reactions mentioned. Use can also be made in this context of variants which are known but not mentioned here in greater detail. The starting substances can also, if desired, be formed in situ in such a way that they are not isolated from the reaction mixture, but immediately reacted further.

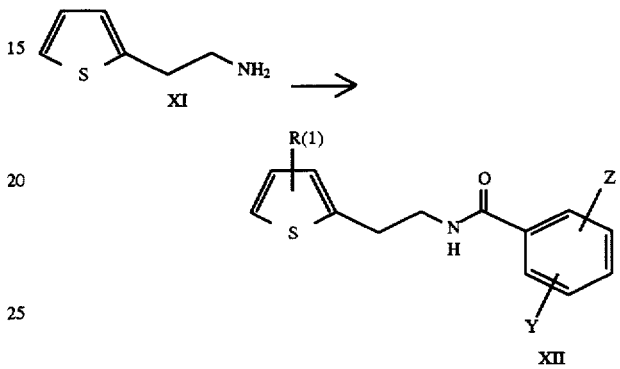

Suitably substituted amines of the formula XI can thus be acylated according to Scheme 1 and subjected to a halosulfonation. Suitable acylating agents for the acylation of amino groups are expediently the alkyl esters, halides (for example chlorides or bromides) or anhydrides of carboxylic acids of the formula R$_4$—COB.

R$_4$ in this context is a benzoic acid derivative. The benzoic acid derivative can in this case be unsubstituted or substituted by one or two identical or different radicals Y and Z having the meaning defined at the outset.

B is a leaving group such as halide, alkoxy having 1, 2, 3 or 4 carbon atoms, trihaloacetate or (C$_1$-C$_4$)-carboxylate. Examples of this are 5-chloro-2-methoxybenzoyl chloride or -benzoic anhydride and -(C$_1$-C$_4$)-alkyl esters or 2,5-difluorobenzoyl chloride. The syntheses of the compound XII are carried out with addition of a tertiary base (such as of pyridine or a trialkylamine) in the presence or absence of an inert solvent, it also being possible for a catalyst, such as dimethylaminopyridine, to be present. The reaction can be achieved at temperatures from approximately 0° C. to 160° C., preferably from 20° to 150° C. Suitable inert solvents are ethers (such as tetrahydrofuran, dioxane), glycol ethers such as ethylene glycol monomethyl or monoethyl ether (methyl glycol or ethyl glycol), ethylene glycol dimethyl ether (diglyme), ketones such as acetone or butanone, nitrites such as acetonitrile, nitro compounds such as nitromethane, esters such as ethyl acetate, amides such as dimethylformamide (DMF) or N-methylpyrrolidone (NMP), hexamethylphosphoramide, sulfoxides such as DMSO, chlorinated hydrocarbons such as dichloromethane, chloroform, hexamethylphosphoramide, sulfoxides such as DMSO, chlorinated hydrocarbons such as dichloromethane, chloroform, trichloroethylene, 1,2-dichloroethane or carbon tetrachloride, and hydrocarbons such as benzene, toluene and xylenes. Furthermore, mixtures of these solvents with one another are also suitable.

Amines XI are in general obtainable by standard processes, for example from thiophene-2-carbaldehydes, which are reacted with nitromethane to give the corresponding nitroolefins, and are then subjected to a reduction, for example with LiAlH₄, and in this process afford XI.

The amines XII acylated according to Scheme 1 can be converted in a known manner according to Scheme 2 into the sulfonamides XIII:

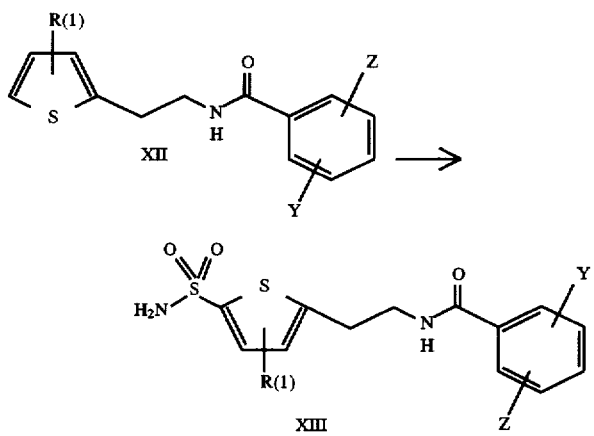

The sulfonamides XIII are prepared by known methods, namely under reaction conditions which are known and suitable for the reactions mentioned. In this case, use can also be made of variants which are known, but not mentioned here in greater detail. The syntheses can be completed, if desired, in one, two or more steps. In particular, processes are preferred in which the acylated amine XII is converted by electrophilic reagents in the presence or absence of inert solvents at temperatures of −10° C. to 120° C., preferably of 0° C. to 100° C., into aromatic sulfonic acids and their derivatives, for example into sulfonyl halides. For example, sulfonations can be carried out with sulfuric acids or oleum, halosulfonations with halosulfonic acids, reactions with sulfuryl halides in the presence of anhydrous metal halides or thionyl halides in the presence of anhydrous metal halides with subsequent oxidations, which are carried out in a known manner, to give aromatic sulfonyl chlorides. If sulfonic acids are the primary reaction products, these can be converted into sulfonyl halides in a known manner by acid halides, such as phosphorus trihalides, phosphorus pentahalides, phosphorus oxychlorides, thionyl halides or oxalyl halides, either directly or by treatment with tertiary amines, such as pyridine or trialkylamines, or with alkali metal or alkaline earth metal hydroxides or reagents which form these basic compounds in situ. The sulfonic acid derivatives are converted into sulfonamides in a manner known from the literature, preferably sulfonyl chlorides are reacted with aqueous ammonia in inert solvents at temperatures from 0° C. to 100° C. Furthermore, aromatic sulfonamides can be synthesized according to processes known from the literature from the acylated amines of the formula XII prepared according to Scheme 1 by reactions with organic reagents of alkali metals or alkaline earth metals in inert solvents and under an inert gas atmosphere at temperatures from −100° C. to 50° C., preferably from −100° C. to 30° C., with sulfur dioxide and subsequent thermal treatment with sulfamic acid.

Depending on the position of the substituents R(1) in the acylated amines XII, the sulfamoyl group can also be introduced into one of the other positions of the thiophene ring, for example into the 4-position if the 5-position is already occupied by R(1).

The compounds I according to the invention and their physiologically acceptable salts can be used for the production of pharmaceutical preparations, in particular by a nonchemical route. In this context, they can be brought into a suitable dose form together with at least one solid or liquid excipient or auxiliary on their own or in combination with other pharmaceuticals having cardiovascular activity, such as calcium antagonists, NO donors or ACE inhibitors. These preparations can be used as pharmaceuticals in human or veterinary medicine.

Possible excipients are organic or inorganic substances which are suitable for enteral (for example oral) or parenteral administration, for example intravenous administration, or topical applications and do not react with the novel compounds, for example water, vegetable oils, benzyl alcohols, polyethylene glycols, glycerol triacetate, gelatin, carbohydrates such as lactose or starch, magnesium stearate, talc, lanolin and petroleum jelly. In particular, tablets, coated tablets, capsules, syrups, juices or drops are used for oral administration, solutions, preferably oily or aqueous solutions, and further suspensions, emulsions or implants, are used for rectal administration, and creams, pastes, lotions, gels, sprays, foams, aerosols, solutions (for example in alcohols such as ethanol or isopropanol, acetonitrile, DMF, dimethylacetamide, 1,2-propanediol or their mixtures with one another or with water) or powders are used for topical application. The compounds I can also be lyophilized and the lyophilizates obtained used, for example, for the production of injection preparations. In particular for topical application, liposomal preparations are also suitable. They contain stabilizers and/or wetting agents, emulsifiers, salts and/or auxiliaries such as lubricants, preservatives, salts for affecting the osmotic pressure, buffer substances, colorants and flavorings and/or aromatic substances. If desired, they can also contain one or more further active compounds, for example one or more vitamins.

The doses which are necessary for the treatment of cardiac arrhythmias with the compounds I depend on whether the therapy is acute or prophylactic. Normally, a dose range of approximately at least 0.1 mg, preferably at least 1 mg, up to at most 100, preferably up to at most 10, mg per kg per day, based on an adult of weight 75 kg, is adequate if prophylaxis is conducted. The dose can in this case be divided as an oral or parenteral individual dose or in up to four individual doses. If acute cases of cardiac arrhythmias are treated, for example in an intensive care unit, parenteral administration can be advantageous. A preferred dose range in critical situations can then be 10 to 100 mg and be administered, for example, as an intravenous continuous infusion.

Suitable experimental animals for the demonstration of such effects on the heart are, for example, mice, rats, guinea-pigs, rabbits, dogs, monkeys or pigs. The compounds can therefore be used as pharmaceutical active compounds in human and veterinary medicine. They can further be used as intermediates for the production of further pharmaceutical active compounds.

According to the invention, in addition to the compounds described in the working examples, the compounds I compiled in the following Table can be obtained:

1) 2-[2-(5-Fluoro-2-methoxybenzoylamino)ethyl]-5-(aminocarbonylaminosulfonyl)thiophene
2) 2-[2-(5-Bromo-2-methoxybenzoylamino)ethyl]-5-(aminocarbonylaminosulfonyl)thiophene
3) 2-[2-(5-Methyl-2-methoxybenzoylamino)ethyl]-5-(aminocarbonylaminosulfonyl)thiophene
4) 2-[2-(5-Fluoro-2-ethoxybenzoylamino)ethyl]-5-(aminocarbonylaminosulfonyl)thiophene
5) 2-[2-(5-Chloro-2-methoxybenzoylamino)ethyl]-5-(aminocarbonylaminosulfonyl)-4-methoxythiophene

9

6) 2-[2-(5-Chloro-2-methoxybenzoylamino)ethyl]-5-(methylaminocarbonylaminosulfonyl)-4-methoxythiophene
7) 2-[2-(5-Chloro-2-methoxybenzoylamino)ethyl]-5-(methylaminocarbonylaminosulfonyl)-4-methylthiothiophene
8) 2-[2-(5-Chloro-2-methoxybenzoylamino)ethyl]-5-(methylaminocarbonylaminosulfonyl)-4-methoxythiophene
9) 2-[2-(5-Chloro-2-methoxybenzoylamino)ethyl]-5-(methylaminocarbonylaminosulfonyl)-4-trifluorothiophene
10) 2-[2-(5-Chloro-2-methoxybenzoylamino)ethyl]-5-(methylaminocarbonylaminosulfonyl)-4-trifluoromethoxy-thiophene
11) 2-[2-(5-Chloro-2-methoxybenzoylamino)ethyl]-5-(aminocarbonylaminosulfonyl)-4-methylthiothiophene
12) 2-[2-(5-Chloro-2-methoxybenzoylamino)ethyl]-5-(aminocarbonylaminosulfonyl)-4-methoxythiophene
13) 2-[2-(5-Chloro-2-methoxybenzoylamino)ethyl]-5-(aminocarbonylaminosulfonyl)-4-trifluorothiophene
14) 2-[2-(5-Chloro-2-methoxybenzoylamino)ethyl]-5-(aminocarbonylaminosulfonyl)-4-trifluoromethoxythiophene
15) 2-[2-(5-Fluoro-2-methoxybenzoylamino)ethyl]-5-(aminothiocarbonylaminosulfonyl)thiophene
16) 2-[2-(5-Bromo-2-methoxybenzoylamino)ethyl]-5-(aminothiocarbonylaminosulfonyl)thiophene
17) 2-[2-(5-Methyl-2-methoxybenzoylamino)ethyl]-5-(aminothiocarbonylaminosulfonyl)thiophene
18) 2-[2-(5-Fluoro-2-ethoxybenzoylamino)ethyl]-5-(aminothiocarbonylaminosulfonyl)thiophene
19) 2-[2-(5-Chloro-2-methoxybenzoylamino)ethyl]-5-(aminothiocarbonylaminosulfonyl)-4-methoxythiophene
20) 2-[2-(5-Chloro-2-methoxybenzoylamino)ethyl]-5-(methylaminothiocarbonylaminosulfonyl)-4-methoxythiophene
21) 2-[2-(5-Chloro-2-methoxybenzoylamino)ethyl]-5-(methylaminothiocarbonylaminosulfonyl)-4-methylthio-thiophene
22) 2-[2-(5-Chloro-2-methoxybenzoylamino)ethyl]-5-(methylaminothiocarbonylaminosulfonyl)-4-methoxythiophene
23) 2-[2-(5-Chloro-2-methoxybenzoylamino)ethyl]-5-(methylaminothiocarbonylaminosulfonyl)-4-trifluorothiophene
24) 2-[2-(5-Chloro-2-methoxybenzoylamino)ethyl]-5-(methylaminothiocarbonylaminosulfonyl)-4-trifluoromethoxythiophene
25) 2-[2-(5-Chloro-2-methoxybenzoylamino)ethyl]-5-(aminothiocarbonylaminosulfonyl)-4-methylthiothiophene
26) 2-[2-(5-Chloro-2-methoxybenzoylamino)ethyl]-5-(aminothiocarbonylaminosulfonyl)-4-methoxythiophene
27) 2-[2-(5-Chloro-2-methoxybenzoylamino)ethyl]-5-(aminothiocarbonylaminosulfonyl)-4-trifluorothiophene
28) 2-[2-(5-Chloro-2-methoxybenzoylamino)ethyl]-5-(aminothiocarbonylaminosulfonyl)-4-trifluoromethoxythiophene

10

EXAMPLES

Example 1

2[-(2-(5-Chloro-2-methoxybenzoylamino)ethyl]-5-(methylaminocarbonylaminosulfonyl)thiophene

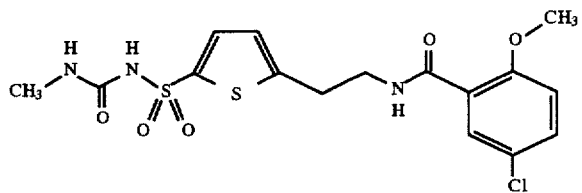

120 mg of powdered NaOH and 141 mg of N-methyltrichloro-acetamide (0.8 mmol) were added to 299 mg (0.8 mmol) of 2-[2-(5-chloro-2-methoxybenzoylamino)ethyl]-5-sulfamoyl-thiophene in 9 ml of DMSO. The mixture was stir 65° C. for 1.5 hours. After cooling, it was stirred into ice water of pH 2. The precipitate was filtered off with suction and taken up in $CH_2Cl_2$, and the solution was washed with water and dried using $MgSO_4$. After evaporating the solvent, a yellow-brown crude product remained which, after treatment with $CH_2Cl_2$/5% methanol, crystallized at −4° C.

165 mg of pure product of m.p.: 160° –161° C. were obtained.

Example 2

2-[2-(5-Chloro-2-methoxybenzoylamino)ethyl]-5-(amino-carbonylaminosulfonyl)thiophene

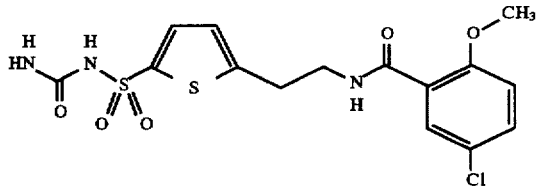

299 mg (0.8 mmol of 2-[2-(5-chloro-2-methoxybenzoylamino)ethyl]-5-sulfamoylthiophene were treated with 448 mg of KOCN and 0.6 ml of triethylamine, and the mixture was then heated to reflux for 4 h. The cooled solution was filtered and evaporated to dryness. The residue was stirred with 40 ml of $H_2O$, 25 ml of triethylamine and 25 ml of ethyl acetate. The organic phase was extracted 3 times with water/1% triethylamine. The combined aqueous phases were acidified with 2N hydrochloric acid. The precipitate formed was stirred in an ice bath for 3 hours and filtered off with suction.

M.p.: 172°–174° C.

Example 3

2-[2-(5-Chloro-2-methoxybenzoylamino)ethyl]-3-methyl-5-(methylaminocarbonylaminosulfonyl)thiophene

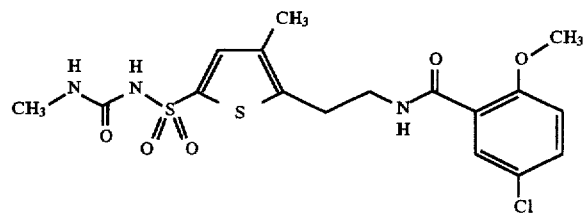

Preparation as in Example 1 from 2-[2-(5-chloro-2-methoxybenzoylamino)ethyl]-3-methyl-5-sulfamoylthiophene and trichloroacetamide. The crude product was purified by stirring in ethyl acetate at 30° C.
M.p.: 185°–187° C.

Example 4

2-[2-(5-Chloro-2-methoxybenzoylamino)ethyl]-3-methyl-5-(aminocarbonylaminosulfonyl)thiophene

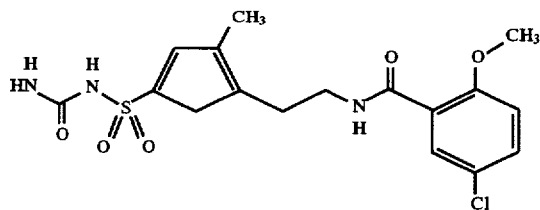

311 mg (0.8 mmol) of 2-[2-(5-chloro-2-methoxybenzoylamino)ethyl]-3-methyl-5-sulfamoylthiophene were treated with 448 mg of KOCN and 0.6 ml of triethylamine, and the mixture was then heated to reflux for 4 h. The cooled solution was filtered and evaporated to dryness. The residue was stirred with 40 ml of $H_2O$, 25 ml of triethylamine and 25 ml of ethyl acetate. The organic phase was extracted 3 times with water/1% triethylamine. The combined aqueous phases were acidified with 2N hydrochloric acid. The precipitate formed was stirred for 3 hours in an ice bath and filtered off with suction.
M.p.: 174°–176° C.

Example 5

2-[2-(5-Chloro-2-methoxybenzoylamino)ethyl]-5-(methyl-aminothiocarbonylaminosulfonyl)thiophene

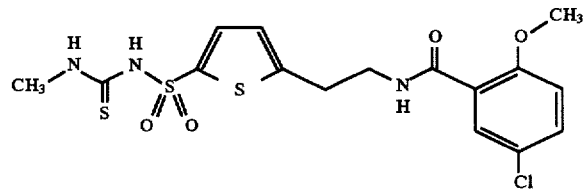

375 mg of 2-[2-(5-chloro-2-methoxybenzoylamino)ethyl]-5-sulfamoylthiophene were dissolved in 3 ml of absolute DMF together with 415 mg of $K_2CO_3$ and 90 mg of methyl isothiocyanate, and the mixture was then stirred for 3 h at 60° C. The cooled solution was introduced into 2N HCl and the resulting precipitate was filtered off with suction. The dried residue was chromatographed on silica gel using the eluent system ethyl acetate/toluene 1:1.
Yield: 228 mg of m.p.: 182°–184° C.

Example 6

2-[2-(5-Chloro-2-methoxybenzoylamino)ethyl]-4-(methyl-aminocarbonylaminosulfonyl)-5-methylthiophene

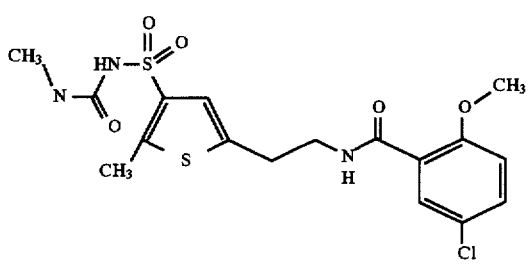

Analogously to Example 1 from 2-[2-(5-chloro-2-methoxybenzoylamino)ethyl]-5-methyl-4-sulfamoylthiophene and trichloroacetamide.
M.p.: 198°–1990° C.

Example 7

2-[2-(5-Chloro-2-methoxybenzoylamino)ethyl]-4-(aminocarbonylaminosulfonyl)-5-methylthiophene Analogously to Example 2 from 2-[2-(5-chloro-2-methoxybenzoylamino)ethyl]-4-sulfamoyl-5-methylthiophene and KOCN.
M.p.: 160°–161° C.
Pharmacological data:
The therapeutic properties of the compounds I can be revealed using the following models:
(1) Action potential duration on the papillary muscle of the guinea-pig ATP deficiency states, as are observed during ischemia in the cardiac muscle cell, lead to a reduction of the action potential duration. They count as one of the causes of so-called reentry arrhythmias, which can cause sudden heart death. The opening of ATP-sensitive K channels as a result of the fall of ATP counts as causal here.

To measure the action potential, a standard microelectrode technique was employed. For this, guinea-pigs of both sexes were killed by a blow to the head, the hearts were removed, and the papillary muscles were separated out and suspended in an organ bath. The organ bath was irrigated with Ringer solution (0.9% NaCl, 0.048% KCl, 0.024% $CaCl_2$, 0.02% $NaHCO_3$ and 0.1% glucose) and aerated with a mixture of 95% oxygen and 5% carbon dioxide at a temperature of 36° C. The muscle was stimulated by means of an electrode using square-wave impulses of 1 V and 1 ms duration and a frequency of 2 Hz. The action potential was derived and recorded by means of a glass microelectrode inserted intracellularly, which was filled with 3 mM KCl solution. The substances to be tested were added to the Ringer solution in a concentration of $2.2 - 10^{-5}$ mol per liter. The action potential was amplified using an amplifier from Hugo Sachs and shown on an oscilloscope. The duration of the action potential was determined at a degree of repolarization of 95% (APD95).

Action potential reductions were produced either by addition of a 1 μM solution of the potassium channel opener Hoe 234 (J. Kaiser, H. Gögelein, Naunyn-Schmiedebergs Arch. Pharm. 1991, 343, R 59) or by addition of 2-deoxyglucose. The action potential-reducing effect of these substances was prevented or reduced by the simultaneous addition of the test substances. Test substances were added to the bath solution as stock solutions in propanediol. The values indicated relate to measurements 30 minutes after addition. Glibenclamide was used in these measurements as a standard. The test concentration in all cases is $2\times10^{-5}$M.

The following values were measured:

| Example No. | APD95-start [ms] | APD95-30 min [ms] |
|---|---|---|
| 1 | 168 ± 15 | 150 ± 13 |
| 2 | 193 | 131 |

(2) Membrane potential on isolated β-cells

The mechanism of action of the hypoglycemic sulfonylureas was elucidated in rough terms. The target organ was the β-cells of the pancreas where increased secretion of the hypoglycemic hormone insulin occurs. The release of insulin was controlled by means of the cell membrane potential. Glibenclamide causes a depolarization of the cell membrane, which promotes insulin release via an increased influx of calcium ions. The extent of this depolarization of the cell membrane ΔU was determined on RINm5F cells, a pancreas tumor cell line, for a few of the compounds according to the invention. The potency of a compound in this model predicts the extent of the hypoglycemic potential of this compound.

Cell culture of RINm5F cells

RINm5F cells were cultured at 37° C. in RPMI 1640 culture medium (Flow), to which 11 mM glucose, 10% (vol/vol) fetal calf serum, 2 mM glutamine and 50 μg/ml of gentamycin were added. For the investigations, the cells were isolated by incubation (about 3 minutes) in a $Ca^{2+}$-free medium which contained 0.25% trypsin, and were stored on ice.

Isolated RINm5F cells were transferred to a Plexiglas chamber on an inverted microscope equipped with a differential interference contrast optical system. Under visual control (400-fold magnification), a fire-polished micropipette with an opening diameter of about 1 μm was set up on the cell with the aid of a micromanipulator. By applying a slight reduced pressure in the patch pipette, a high electrical seal was first produced between the glass and cell membrane and then broken by increasing the reduced pressure of the membrane spot under the measuring pipette. In this whole cell configuration, the cell potential was recorded with the aid of a patch clamp amplifier (L/M EPC 7) and the whole cell current was measured by applying a voltage ramp. Solutions: The patch pipette was filled with KCl solution (in mmol per liter): 140 KCl, 10 NaCl, 1.1 $MgCl_2$, 0.5 EGTA, 1 Mg-ATP, 10 HEPES, pH=7.2, and NaCl solution was in the bath (in mmol per liter): 140 NaCl, 4.7 KCl, 1.1 $MgCl_2$, 2 $CaCl_2$, 10 HEPES, pH=7.4. Stock solutions of the test substances (concentration 100 zmol) in dimethyl sulfoxide (DMSO) and corresponding dilutions in NaCl solution were prepared. DMSO on its own had no effect on the cell potential. In order to stabilize the cell potential under control conditions, the opener for ATP-sensitive $K^+$channels, diazoxide, (100 μmol) was added to the bath solution in all experiments. All experiments were carried out at 34°±1° C.

(c) Results (The concentration of the compounds according to the invention in the experiments was $10^{-5}$ mol per liter)

| Example No. | ΔU (mV) |
|---|---|
| 1 | 5 (blank value: −80 mV) |
| 2 | 4 (blank value: −79 mV) |

We claim:

1. A thiophenesulfonylurea or a thiophenesulfonylthiourea of the formula I

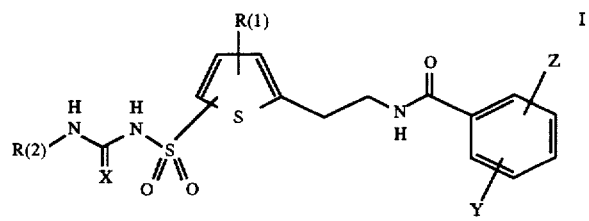

wherein,

R(1) is selected from the group consisting of hydrogen, halogen, alkyl having 1 or 2 carbon atoms, alkoxy having 1 or 2 carbon atoms, mercaptoalkyl having 1 or 2 carbon atoms, fluoroalkoxy having 1 or 2 carbon atoms, and fluoroalkyl having 1 or 2 carbon atoms;

R(2) is selected from the group consisting of hydrogen, alkyl having 1 or 2 carbon atoms, and trifluoromethyl;

X is selected from the group consisting of oxygen and sulfur;

Y and Z are identical or different and are selected from the group consisting of hydrogen, F, Cl, Br, I, alkyl having 1 or 2 carbon atoms and alkoxy having 1 or 2 carbon atoms or a psysiologically acceptable salt of formula I.

2. A compound of the formula I as claimed in claim 1 or a salt thereof, in which;

R(1) is hydrogen, alkyl having 1or 2 carbon atoms or alkoxy having 1 or 2 carbon atoms;

R(2) is hydrogen or methyl;

X is oxygen or sulfur;

Y and Z are different from one another and are flourine, chlorine, or alkoxy having 1 or 2 carbon atoms.

3. A compound of the formula I as claimed in claim 1 or a salt thereof, in which:

R(1) is hydrogen or alkyl having 1 or 2 carbon atoms;

R(2) is hydrogen or methyl;

X is oxygen;

Y and Z are different from one another and are fluorine, chlorine, methoxy or ethoxy.

4. A compound of the formula I as claimed in claim 1 or a salt thereof, in which:

R(1) is hydrogen or alkyl having 1 or 2 carbon atoms;

R(2) is hydrogen or methyl;

X is sulfur;

Y and Z are different from one another and are fluorine, chlorine, methoxy or ethoxy.

5. A process for the preparation of a compound I as claimed in claim 1, which comprises (a) reacting an aromatic sulfonamide of the formula II

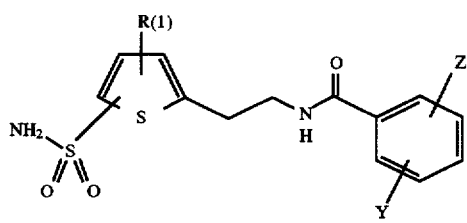

or its salt of the formula III

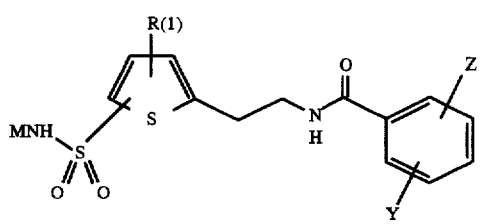

in which R(1), Y and Z have the meanings indicated in claim 1 and in which M is an alkali metal, alkaline earth metal, ammonium or tetraalkylammonium ion, with R(2)-substituted isocyanates of the formula IV

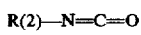 IV in which R(2) has the meaning indicated in claim 1, to form a thiophenesulfonylurea of the formula I; or (b) reacting an aromatic thiophenesulfonamide of the formula II or the salt of the formula III with trialkylsilyl isocyanate or silicon tetraisocyanate to form a silicon-substituted thiophenesulfonylurea and cleaving said silicon-substituted tetraisocyanate to form a thiophenesulfonylurea of the formula I wherein R(2) is H; or (c) reacting an aromatic thiophenesulfonamide of the formula II or its salt of the formula III with an R(2)-substituted trichloroacetamide of the formula V

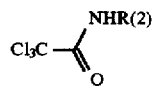 V in the presence of a base to form a thiophenesulfonylurea of the formula I wherein X is O; or (d) reacting an aromatic sulfonamide of the formula II or its salt of the formula III with an R(2)-substituted isothiocyanate of the formula VI

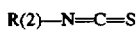 VI;

to form a thiophenesulfonylthiourea of the formula I wherein X is S; or (e) reacting a thiophenesulfonyl halide of the formula VII

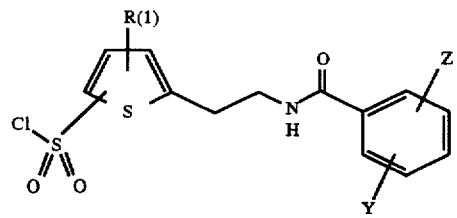

with an R(2)-substituted urea or R(2)-substituted bis (trialkylsilyl)urea to form a thiophenesulfonylurea of the formula I wherein X is O; or (f) reacting an amine of the formula R(2)—NH₂ with a thiophenesulfonyl isocyanate of the formula VIII

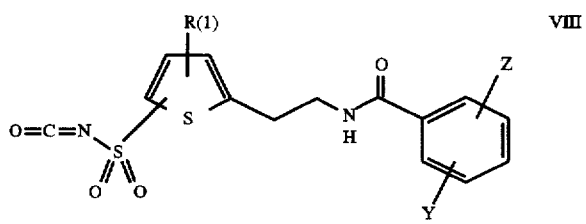

to form a thiophenesulfonylurea urea of the formula I wherein X is O; or (g) reacting an amine of the formula R(2)—NH₂ with a thiophenesulfonyl isothiocyanate of the formula IX

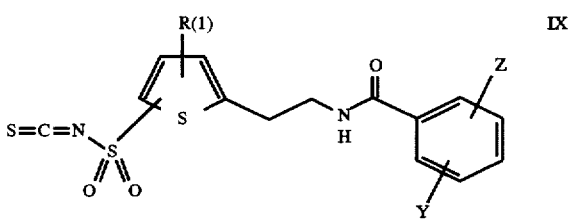

to form a thiophenesulfonylthiourea of the formula I wherein X is S; or (h) oxidizing a benzenesulfenyl- or -sulfinylurea to give a thiophenesulfonylurea of the formula I wherein X is O.

6. A method for the treatment of ischemic conditions of the heart, weakened cardiac power, or cardiac arrhythmias comprising administering an effective amount of a thiophenesulfonylurea or thiophenesulfonylthiourea of the formula I as claimed in claim 1.

7. A method for the prevention of sudden heart death or the improvement of heart function after heart transplantation comprising administering an effective amount of the thiophenesulfonylurea or thiophenesulfonylthiourea of the formula I as claimed in claim 1, or a salt thereof.

8. A method of investigating the inhibition of ATP-sensitive potassium channels comprising administering an effective amount of the thiophenesulfonylurea or thiophenesulfonylthiourea of the formula I as claimed in claim 1, or a salt thereof as a diagnostic agent.

9. A pharmaceutical composition comprising an effective amount of a compound of the formula I as claimed in claim 1 or a salt thereof.

10. A process for the preparation of a compound Ia

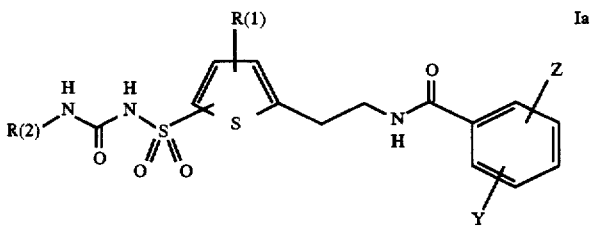

wherein

R(1) is selected from the group consisting of hydrogen, halogen, alkyl having 1 or 2 carbon atoms, alkoxy having 1 or 2 carbon atoms, mercaptoalkyl having 1 or 2 carbon atoms, fluoroalkoxy having 1 or 2 carbon atoms, and fluoroalkyl having 1 or 2 carbon atoms;

R(2) is selected from the group consisting of hydrogen, alkyl having 1 or 2 carbon atoms, alkoxy having 1 or 2 carbon atoms, and trifluoromethyl;

Y and Z are identical or different and are selected from the group consisting of hydrogen, F, Cl, Br, I, alkyl having 1 or 2 carbon atoms and alkoxy having 1 or 2 carbon atoms;

which comprises the steps of desulfurizing a compound of the formula Ib

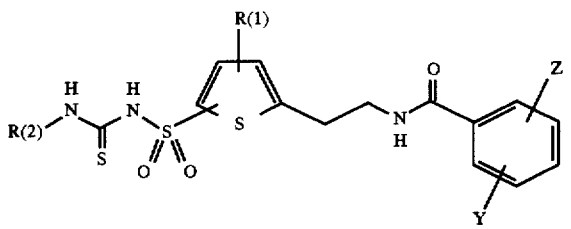

Ib

11. A process for the preparation of a compound Ia as claimed in claim 10 wherein a compound of the formula Ib is reacted with oxides or salts of heavy metals.

12. A process for the preparation of a compound Ia as claimed in claim 10 wherein a compound of the formula Ib is reacted with an oxidant.

13. A process for the preparation of a compound Ia as claimed in claim 12 wherein said oxidant is selected from the group consisting of hydrogen peroxide, sodium peroxide, and nitrous acid.

14. A process for the preparation of a compound Ia as claimed in claim 10 wherein a compound of the formula Ib is reacted with phosgene or phosphorus pentachloride and then hydrolyzed to form said compound Ia.

* * * * *